(12) United States Patent
Ogawa

(10) Patent No.: US 6,901,157 B2
(45) Date of Patent: May 31, 2005

(54) ULTRASONIC DIAGNOSTIC APPARATUS

(75) Inventor: Eiji Ogawa, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 666 days.

(21) Appl. No.: 10/035,256

(22) Filed: Jan. 4, 2002

(65) Prior Publication Data
US 2002/0094115 A1 Jul. 18, 2002

(30) Foreign Application Priority Data

Jan. 15, 2001 (JP) ........................................ 2001-005994
Jan. 15, 2001 (JP) ........................................ 2001-005995

(51) Int. Cl.$^7$ ................................................. G06K 9/00
(52) U.S. Cl. .................. 382/128; 600/437; 128/200.16
(58) Field of Search ................................ 382/128, 129, 382/130, 131, 132, 133, 134; 600/407, 437, 439, 443; 128/200.16, 915, 916

(56) References Cited

U.S. PATENT DOCUMENTS

| 4,679,565 A | * | 7/1987 | Sasaki .......................... 600/437 |
| 5,179,954 A | * | 1/1993 | Arima et al. ................ 600/443 |
| 5,497,776 A | * | 3/1996 | Yamazaki et al. ........... 600/445 |
| 6,416,476 B1 | * | 7/2002 | Ogasawara et al. ......... 600/443 |
| 6,540,676 B2 | * | 4/2003 | Kamiyama ................... 600/437 |

FOREIGN PATENT DOCUMENTS

| JP | 2-21262 | 5/1990 |
| JP | 5-240919 | 9/1993 |
| JP | 6-205780 | 7/1994 |

* cited by examiner

Primary Examiner—Bhavesh M. Mehta
Assistant Examiner—Abolfazl Tabatabai
(74) Attorney, Agent, or Firm—Sughrue Mion, PLLC

(57) ABSTRACT

An ultrasonic diagnostic apparatus in which the optimum transmission/reception conditions and image processing conditions can be easily set for each body part of an object to be inspected. The ultrasonic diagnostic apparatus includes an ultrasonic transmitting and receiving unit; an image processing unit for executing image processing of image data by using image processing condition parameters; an information input unit to be employed for inputting information of object concerned with the object to be inspected, a parameter memory unit for storing the image processing condition parameters in correspondence with the information of object; a control unit for reading out the image processing condition parameters corresponding to the information of object input by employing the information input unit to supply the read-out parameters to the image processing unit; and a display unit for displaying an image.

27 Claims, 11 Drawing Sheets

ULTRASONIC DIAGNOSTIC APPARATUS

BACKGROUND OF THE INVENTION

1. Field of the Invention

The present invention relates to an ultrasonic diagnostic apparatus wherein ultrasonic waves are transmitted to an object to be inspected and echo waves reflected from the object are received so that a medical diagnosis is made on the basis of an image obtained from information contained in the received echo waves.

2. Description of a Related Art

In general, the qualities of an ultrasonic diagnostic image depend on the transmission/reception conditions of ultrasonic waves, the processing conditions of the image, etc. As the ultrasonic transmission/reception conditions, a center frequency, a bandwidth, a focussing position, transmission power, reception sensitivity, etc. of the ultrasonic waves are mentioned. As the image processing conditions, brightness and contrast in an image displayed on a display device are mentioned. Regarding these conditions, appropriate values would exist for every body part of an object to be inspected.

Heretofore, the parameters of the ultrasonic transmission/reception conditions and image processing conditions, etc. have been manually input from an operation panel mounted on the ultrasonic diagnostic apparatus, and they have been reset and optimized each time when an image has been obtained and displayed. Adjustments for such optimization of the parameters must be made while the object is being scanned with an ultrasonic probe, and they are very laborious and troublesome operations for a person such as a doctor who handles the ultrasonic diagnostic apparatus.

Meanwhile, Japanese patent application publication (post examination) JP-B-2-21262 discloses an ultrasonic diagnostic apparatus in which the maximum value and minimum value of an ultrasonic echo signal are detected, and the ultrasonic image of any designated body part is displayed by automatically changing the gradation from the zero gradation to the maximum gradation on the basis of the detected values. However, a gradation control process proper for each individual body part can not be executed merely by automatically changing the gradation of the ultrasonic image indiscriminately from the zero gradation to the maximum gradation.

It is also considered to preset nearly appropriate conditions for every body part of the object to be inspected, and to set the transmission/reception conditions and the image processing conditions on the basis of the preset conditions and analytical information obtained from the image. According to this technique, the ultrasonic image can be displayed by employing the appropriate transmission/reception conditions and image processing conditions for each image. However, since the analysis of the image is made within a predetermined image region, the determined conditions might deviate from the optimum conditions when a region desired to be observed is somewhat discrepant from the analyzed region.

In this regard, Japanese patent application laid-open JP-A-5-240919 discloses a radiation image reproduction apparatus wherein an image signal expressive of a radiation image is reproduced through image processing. According to the apparatus, when a desired region of interest (ROI) is set on the radiation image, the image processing of the radiation image within the region can be executed by a simple operation. However, the radiation image reproduction apparatus executes the image processing for static image data already acquired, and the technique does not cope with a system which acquires and displays a dynamic image as in the ultrasonic diagnostic apparatus.

Besides, Japanese patent application laid-open JP-A-6-205780 discloses an ultrasonic image processing apparatus in which the degree of the contrast of a region of interest is searched for, and contrast intensification suited to the region can be always effected. However, a gradation control process proper for each individual body part cannot be executed merely by executing the contrast intensification process indiscriminately in the region of interest.

SUMMARY OF THE INVENTION

The present invention has been made in view of such problems. The first object of the present invention is to provide an ultrasonic diagnostic apparatus in which optimum transmission/reception conditions and the image processing conditions can be easily set for each individual body part of an object to be inspected. Besides, the second object of the present invention is to provide an ultrasonic diagnostic apparatus in which transmission/reception conditions and image processing conditions optimizing an image in a region of interest within a screen can be easily set for each individual body part of an object to be inspected.

In order to accomplish the objects of the present invention, an ultrasonic diagnostic apparatus according to the first aspect of the present invention comprises an ultrasonic transmitting and receiving unit for transmitting ultrasonic waves to an object to be inspected and receiving echo waves reflected from the object; an image processing unit for executing image processing of image data, which is obtained on the basis of the echo waves received by the ultrasonic transmitting and receiving unit, by using image processing condition parameters; an information input unit to be employed for inputting information of object concerned with the object to be inspected; a parameter memory unit for storing the image processing condition parameters to be used in the image processing unit, in correspondence with the information of object; a control unit for reading out the image processing condition parameters, which correspond to the information of object input by employing the information input unit, from the parameter memory unit so as to supply the read-out parameters to the image processing unit; and a display unit for displaying an image on the basis of the image data subjected to the image processing in the image processing unit.

According to the above construction, ultrasonic transmissions/receptions or image processing can be executed in accordance with the parameters concerned with transmission/reception conditions or image processing conditions previously stored in the parameter memory unit in correspondence with body parts of the object to be inspected. Therefore, optimum transmission/reception conditions or image processing conditions for the particular body part can be easily set by inputting the information of object, and the image suited for a diagnosis can be efficiently obtained.

Further, an ultrasonic diagnostic apparatus according to the second aspect of the present invention comprises an ultrasonic transmitting and receiving unit for transmitting ultrasonic waves to an object to be inspected and receiving echo waves reflected from the object; a region setting unit to be employed for setting a desired region within a displayed image; an image analysis unit for analyzing image data obtained on the basis of the echo waves received by the ultrasonic transmitting and receiving unit, as to the desired region set by employing the region setting unit; an image processing unit for executing image processing of the image data obtained on the basis of the echo waves received by the ultrasonic transmitting and receiving unit; an information input unit to be employed for inputting information of object concerned with the object to be inspected or image processing rule information concerned with a rule of the image processing; a parameter memory unit for storing parameters concerned with transmission/reception conditions to be used in the ultrasonic transmitting and receiving unit or image processing conditions to be used in the image processing unit, in correspondence with the information of object or the image processing rule information; a control unit for controlling transmission/reception operation of the ultrasonic transmitting and receiving unit or the image processing operation of the image processing unit, in accordance with analytical results in the image analysis unit and the parameters corresponding to the information of object or the image processing rule information input to the information input unit; and a display unit for displaying an image on the basis of the image data subjected to the image processing in the image processing unit.

According to the above construction, the ultrasonic transmissions/receptions or the image processing is executed in accordance with the analytical results of the image data in the region of interest and the parameters corresponding to the input information of object or the image processing rule information. Therefore, the transmission/reception conditions and image processing conditions which optimize the image in the region of interest within a screen can be easily set as to each of the body parts of the object to be inspected, and the image suited for a diagnosis can be efficiently obtained.

DESCRIPTION OF THE PREFERRED EMBODIMENTS

Figure 1:
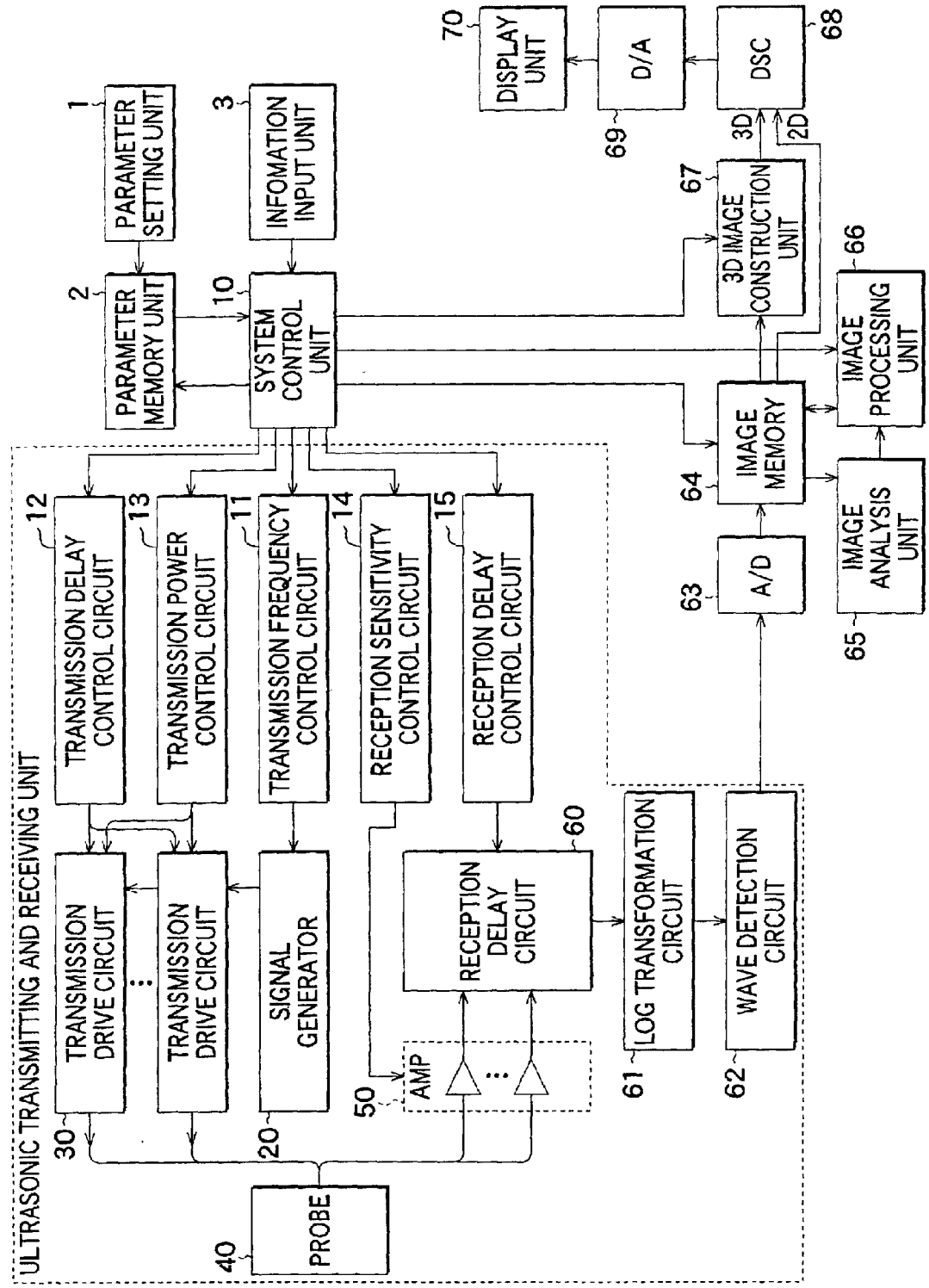
FIG. 1 is a block diagram showing the construction of an ultrasonic diagnostic apparatus according to the first embodiment of the present invention.

Now, embodiments of the present invention will be described in detail with reference to the drawings. Incidentally, the same reference numerals and signs will be assigned to the same constituents, which shall not be repeatedly explained.

FIG. 1 is a block diagram showing the construction of an ultrasonic diagnostic apparatus according to the first embodiment of the present invention. As shown in FIG. 1, the ultrasonic diagnostic apparatus includes a system control unit 10 which controls the whole system, and a transmission frequency control circuit 11, a transmission delay control circuit 12, a transmission power control circuit 13, a reception sensitivity control circuit 14 and a reception delay control circuit 15 which perform the controls of the transmission/reception conditions of ultrasonic waves in an ultrasonic transmitting and receiving unit under the control of the system control unit 10.

Also connected to the system control unit 10 is a parameter memory unit 2 to which a parameter setting unit 1 is connected, and an information input unit 3. Parameters for determining the transmission/reception conditions of the ultrasonic waves and the processing conditions of an image are preset in correspondence with the body parts of an object to be inspected by employing the parameter setting unit 1. Thus, the optimum parameter sets for the respective body parts of the object are stored in the parameter memory unit 2 in correspondence with items of the information of object expressive of the body parts. When an ultrasonic diagnosis is made, ultrasonic transmission/reception and image processing are executed by using an optimum parameter set which is selected from the optimum parameter sets already preset for the body parts of the object, on the basis of information of object which is input to the information input unit 3. The information of object represents, for example, one of the body parts such as liver, heart and so on of a human or a test phantom as the object to be inspected.

In order to transmit and receive the ultrasonic waves, the ultrasonic diagnostic apparatus according to this embodiment includes a signal generator 20 which generates a signal for the transmission, a plurality of transmission drive circuits 30 which amplify the signal and afford necessary delay times thereto so as to output drive signals, a probe 40 which transmits the ultrasonic waves to the object to be inspected on the basis of the drive signals and which receives the echo waves reflected from the object and outputs detection signals, a plurality of amplifiers 50 which amplify the detection signals, a reception delay circuit 60 which affords desired delays to the detection signals, a log transformation circuit 61 which performs the logarithmic transformations of the detection signals, and a wave detection circuit 62 which performs the wave detections of the detection signals.

The probe 40 includes a unidimensional or two-dimensional ultrasonic transducer array which is configured of a plurality of ultrasonic transducers. The ultrasonic transducer may well be a piezoelectric device which is made of, for example, piezoelectric ceramics typified by PZT (Pb (lead) titanate zirconate) ceramics or a piezoelectric high polymer typified by PVDF (polyvinyl difluoride). Further, a two-dimensional sensor array of photodetection mode may well be employed for the reception. Incidentally, the two-dimensional sensor array of photodetection mode will be explained in detail later.

In the transmission circuits, the transmission frequency control circuit 11 controls the center frequency and frequency band of the signal to be output from the signal generator 20. Besides, the transmission delay control circuit 12 controls the delay times of the drive signals to be output from the plurality of transmission drive circuits 30. Thus, the plurality of ultrasonic transducers included in the probe 40 transmits the ultrasonic waves which have phase differences corresponding to the time differences of the drive signals, toward the object to be inspected, respectively. An ultrasonic beam having a specified transmission focus is formed by constructing the wave fronts of such plurality of ultrasonic waves. Further, the transmission power control circuit 13 controls the amplitudes of the drive signals to be output from the plurality of transmission drive circuits 30, whereby the transmission powers of the ultrasonic waves are controlled.

In the reception circuits, the reception sensitivity control circuit 14 controls the gains of the plurality of amplifiers 50, whereby reception sensitivities are controlled. Besides, the reception delay control circuit 15 controls the delay times of the detection signals in the reception delay circuit 60. The output signals of the reception delay circuit 60 are subjected to the logarithmic transformations by the log transformation circuit 61, and to the wave detections by the detection circuit 62. Thereafter, the detected waves are converted by an A/D conversion circuit 63 into digital image data, which is stored in an image memory 64.

The image data thus obtained is subjected to the image processing in an image processing unit 66. A normalization process, a nonlinear gradation control process, a response control process, scale-up/down and interpolation processes, etc. correspond to the image processing. The system control unit 10 reads out of the parameter memory unit 2 the parameters corresponding to such a body part of the object to be inspected that is expressed by the information of object input to the information input unit 3, and it controls the image processing operation of the image processing unit 66 on the basis of the parameters read out. Alternatively, the system control unit 10 may well control at least one of the image processing operation of the image processing unit 66 and the transmission/reception operation. Further, it is also allowed to transmit and receive the ultrasonic waves by using the parameter set which has been already preset for every body part, and to analyze the acquired image data and calculate normalization parameters in an image analysis unit 65. In this case, in the image processing unit 66, a normalization process is executed by using the calculated normalization parameters in accordance with normalization rule preset for every body part and stored in the parameter memory unit 2, and the other image processing is thereafter executed by using the parameter set stored in the parameter memory unit 2. By the way, in case of displaying a three-dimensional image, in a three-dimensional image construction unit 67 generates voxel data, which is data about a certain volume, on the basis of a plurality of tomographic data stored in the image memory 64.

Further, in a DSC (digital scan converter) 68, image data obtained by any one of various scanning modes such as sector scan, linear scan and so on is converted into image data for use in the scanning in a TV (television) signal, so as to become observable with an ordinary monitor. Besides, a frame rate is adjusted in the DSC 68. The image data converted by the DSC 68 is further converted by a D/A conversion circuit 69 into an analog signal, which is used for displaying the image on a display unit 70. The display unit 70 should desirably be capable of displaying a color image. In this embodiment, the image memory 64, image analysis unit 65 and image processing unit 66 are interposed between the A/D conversion circuit 63 and the DSC 68, thereby to decrease the quantity of data at the normalization stage. Alternatively, they may well be interposed between the DSC 68 and the D/A conversion circuit 69.

Next, there will be described the first example of the operation of the ultrasonic diagnostic apparatus according to the first embodiment of the present invention.

At first, when an operator inputs information of object concerned with an object to be inspected and diagnosed to the information input unit 3, image processing condition parameters stored in the parameter memory unit 2 in correspondence with the information of object beforehand are read out by the system control unit 10.

Subsequently, the transmission/reception operations of ultrasonic waves are started in compliance with the instruction of the operator. The transmission drive circuits 30 generate drive signals on the basis of a signal generated by the signal generator 20, and supply them to the transmitting ultrasonic transducers included in the probe 40. The transmitting ultrasonic transducers transmit ultrasonic waves toward the object to be inspected, and echo waves reflected from the object are received and transduced into detection signals by the receiving ultrasonic transducers included in the probe 40. The detection signals are amplified by the plurality of amplifiers 50, and are afforded desired delays by the reception delay circuit 60. Further, the detection signals are subjected to logarithmic transformations by the log transformation circuit 61 and to wave detections by the wave detection circuit 62, whereupon the resulting signals are converted into digital image data by the A/D conversion circuit 63.

The image data thus obtained are accumulated in the image memory 64 in frame units. The accumulated image data are subjected to image processing every frame in the image processing unit 66 in accordance with the image processing condition parameters read out of the parameter memory unit 2, whereupon the processed data are accumulated in the image memory 64 again.

Here, the parameter memory unit 2 may well store a plurality of image processing condition parameter sets (for example, image processing condition parameter sets A, B and C) in correspondence with one item of the information of object. In this case, the operator not only inputs the information of object to the information input unit 3, but also selects that one of the plurality of image processing condition parameter sets which corresponds to the input information of object. By way of example, the operator inputs the information of object for selecting "liver" as the body part, and the operator thereafter inputs information for selecting the image processing condition parameter set B.

Further, it is also allowed to analyze the accumulated image data and calculate normalization parameters in the image analysis unit 65, and to execute in the image processing unit 66 a normalization process by the use of the calculated normalization parameters in accordance with normalization rule preset for every body part and stored in the parameter memory unit 2, followed by the execution of the other image processing. The analysis in the image analysis unit 65 is made by extracting certain frame data from among data being scanned. Regarding the normalization processing for the subsequent successive frames, the calculated normalization parameters may well be used as they are.

Here, the parameter memory unit 2 may well store a plurality of normalization rules in correspondence with one item of the information of object. In this case, the operator selects one of the plurality of normalization rules which corresponds to the information of object input to the information input unit 3.

Next, there will be described the second example of the operation of the ultrasonic diagnostic apparatus according to the first embodiment of the present invention.

When an operator inputs information of object concerned with an object to be inspected and diagnosed to the information input unit 3, transmission/reception condition parameters and image processing condition parameters stored in the parameter memory unit 2 in correspondence with the information of object beforehand are read out by the system control unit 10.

In accordance with the transmission/reception condition parameters read out, the transmission frequency control circuit 11 controls the center frequency and frequency band of a signal to be generated by the signal generator 20, the transmission delay control circuit 12 controls the delay times of drive signals to be output from the transmission drive circuits 30, and the transmission power control circuit 13 controls the amplitudes of the drive signals to be output from the transmission drive circuits 30. Besides, the reception sensitivity control circuit 14 controls the gains of the amplifiers 50, and the reception delay control circuit 15 controls the delay times of detection signals in the reception delay circuit 60. In this manner, the transmission/reception conditions of ultrasonic waves, such as a center frequency, a bandwidth, a focussing position, transmission power, and reception sensitivity thereof, are set in accordance with the transmission/reception condition parameters, and the ultrasonic waves are transmitted and received under the transmission/reception conditions.

Image data obtained by subjecting the detection signals to A/D conversions are accumulated in the image memory 64 in frame units. The accumulated image data are subjected to image processing every frame in the image processing unit 66 in accordance with the image processing condition parameters read out of the parameter memory unit 2, whereupon the processed data are accumulated in the image memory 64 again.

Here, the parameter memory unit 2 may well store a plurality of image processing condition parameter sets (for example, image processing condition parameter sets A, B and C) and a plurality of transmission/reception condition parameter sets (for example, transmission/reception condition parameter sets X, Y and Z) in correspondence with one item of the information of object. In this case, the operator not only inputs the information of object to the information input unit 3, but also selects one of the plurality of image processing condition parameter sets corresponding to the input information of object, as well as selects one of the plurality of transmission/reception condition parameter sets corresponding to the input information of object. By way of example, the operator inputs the information of object for selecting "liver" as the body part, and the operator thereafter inputs information for selecting the image processing condition parameter set B, and information for selecting the transmission/reception condition parameter set Y.

Further, as in the first example, a normalization process may well be executed in the image processing unit 66 in accordance with a normalization rule stored in the parameter memory unit 2, by the use of normalization parameters calculated in the image analysis unit 65.

Next, conditions which can be set by various parameters will be described in detail. A center frequency and a bandwidth will be first described as the transmission/reception conditions of ultrasonic waves.

In a case where the body part of an object to be inspected and diagnosed is near to the surface of the object, even ultrasonic waves at a frequency of, for example, approximately 10 MHz do not attenuate appreciably. On the other hand, in a case where the body part of an object to be inspected and diagnosed is far from the surface of the object, the ultrasonic waves at the frequency of approximately 10 MHz attenuate drastically. In this case, therefore, the center frequency and the bandwidth are respectively set at, for example, approximately 3.5 MHz and approximately 5–6 MHz, respectively.

Secondly, a focussing position will be described. Since the individual body parts of an object to be inspected differ in distances from the surface of the object, perpendicular depth from a probe where a transmission beam is to be focussed needs to be changed depending upon the body parts. When phased array transducers are employed, the focussing position can be set by controlling the number of transmitting elements and the delay times thereof. The parameter may be divided in several stages such as "shallow", "medium" and "deep", or it may well be designated by actual dimensions such as "within 5 cm", "5–10 cm" and "10–20 cm".

A transmission power can be set by the voltage value of a drive signal which is applied to each transducer. The parameter may be divided in several stages such as "low", "medium" and "high" or in ten stages, or it may well be designated by the normalized value of a voltage which is to be afforded, such as % indication.

Besides, a reception sensitivity can be altered by controlling the gain of each amplifier in the reception circuits. The gain of each amplifier can be set in accordance with a distance from a surface of the object to a body part to be diagnosed. The parameter may divide the body part desired to be observed, in several stages such as "shallow", "medium" and "deep", or it may well be designated by actual dimensions such as "within 5 cm", "5–10 cm" and "10–20 cm". The processing gains of detection signals corresponding to a designated region are heightened on the basis of the parameter.

A gradation control process will be first described as one of the image processing conditions. Various gradation control processes including nonlinear transformations can be executed in such a way that data are transformed by employing lookup tables (LUTs) each of which prescribes the relationship between input data and output data. Besides, an image effective for a diagnosis can be offered in such a way that various sorts of LUTs are prepared and are properly used in accordance with body parts.

Figure 2A:
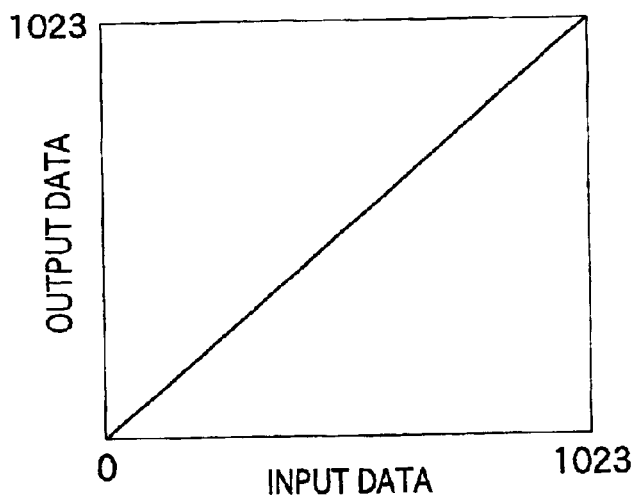
FIGS. 2A to 2C are diagrams each showing an example of a reference lookup table.
Figure 2B:
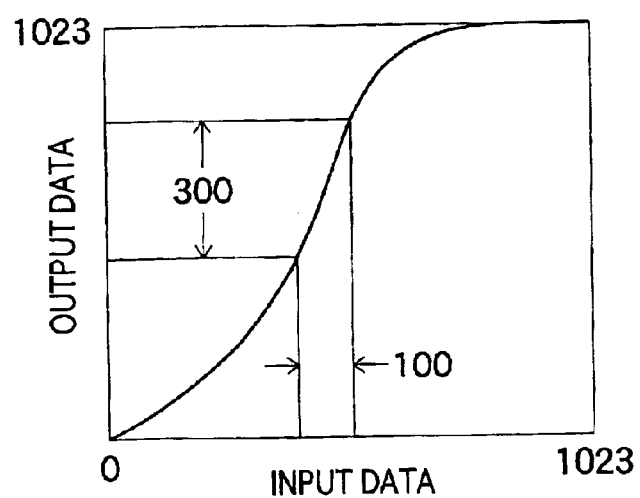
Figure 2C:
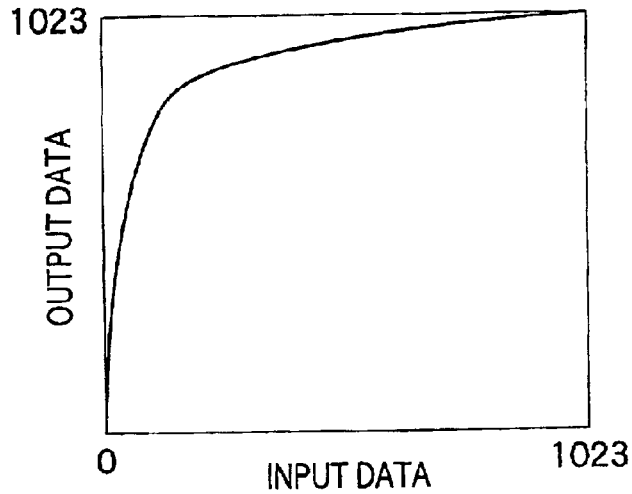

Employable as the LUTs are, for example, reference LUTs as shown in FIGS. 2A to 2C. FIG. 2A shows a linear transformation in which values of input data and values of output data become equal. FIG. 2B shows the nonlinear transformation in which a contrast in an intermediate intensity region is emphasized, where the contrast of output data is expanded about 3 times as large as the contrast of input data in the intermediate intensity region. FIG. 2C shows the nonlinear transformation in which a contrast in a low intensity region is emphasized.

Figure 3A:
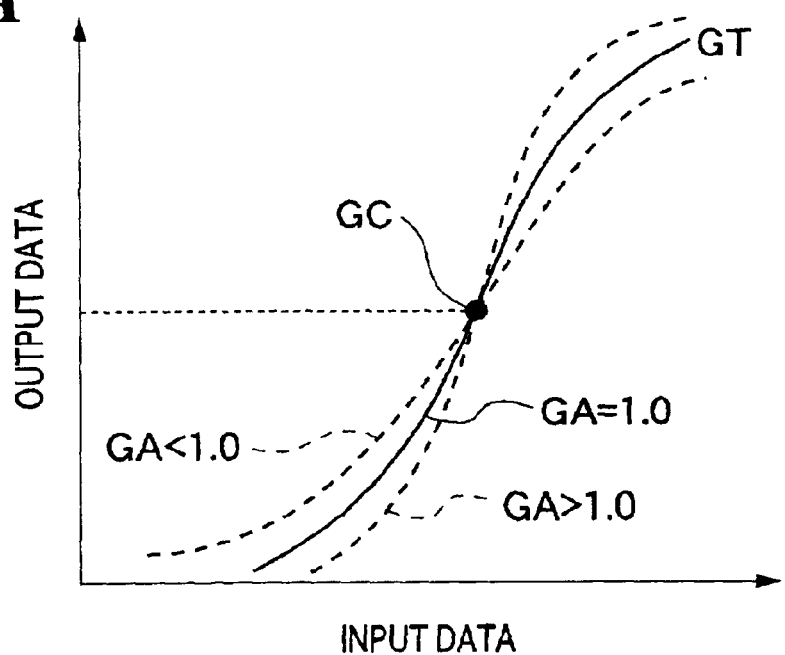
FIGS. 3A and 3B are diagrams showing the gyration and translation of a reference line in a reference lookup table, respectively.
Figure 3B:
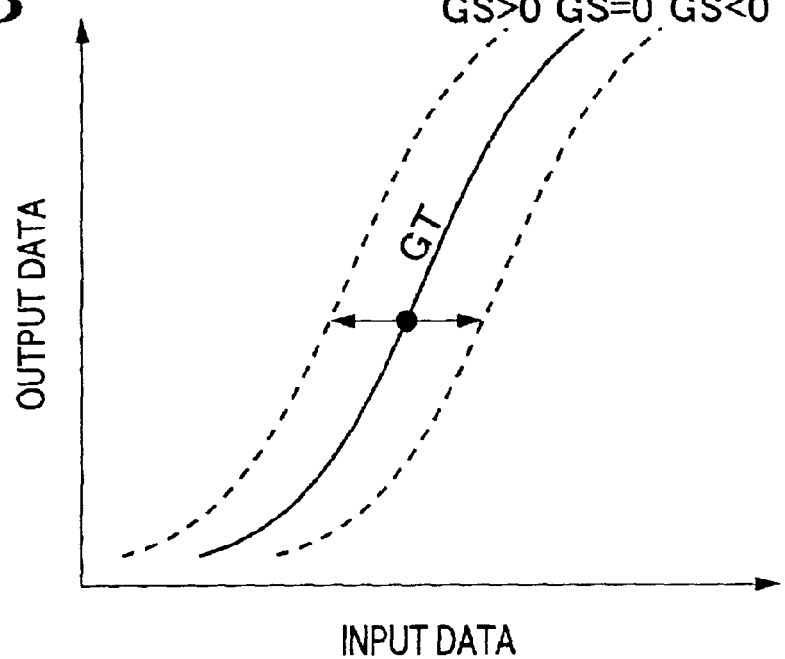

Further, as shown in FIG. 3A or 3B, an LUT in which a reference line in a reference LUT is gyrated or translated may well be employed. FIG. 3A shows the example in which the reference line is gyrated, where transformation characteristics are determined by the parameters of a gradation type (GT), a gyration center (GC) and a gyration amount (GA). FIG. 3B shows the example in which the reference line is translated, where transformation characteristics are determined by the parameters of a gradation type (GT) and a gradation shift amount (GS).

Secondly, a response control process will be described. An unsharp mask process and a differentiation process are included in the response control process. It is also possible to decompose data into multiple resolutions and thereafter process them for reconstruction, and to execute a process in which the nonlinearity tables of respective densities are combined.

The unsharp mask process is expressed by the following equation:

$$QL(x, y)=Q(x, y)+K(Q(x, y))\times[Q(x, y)-Qus(x, y)]$$

where signs Q, Qus and QL denote an original image, an unsharp image and a processed image obtained by the transmissions/receptions of the ultrasonic waves, respectively, and letter K denotes a weighting factor which determines the degree of emphasis.

Figure 4A:
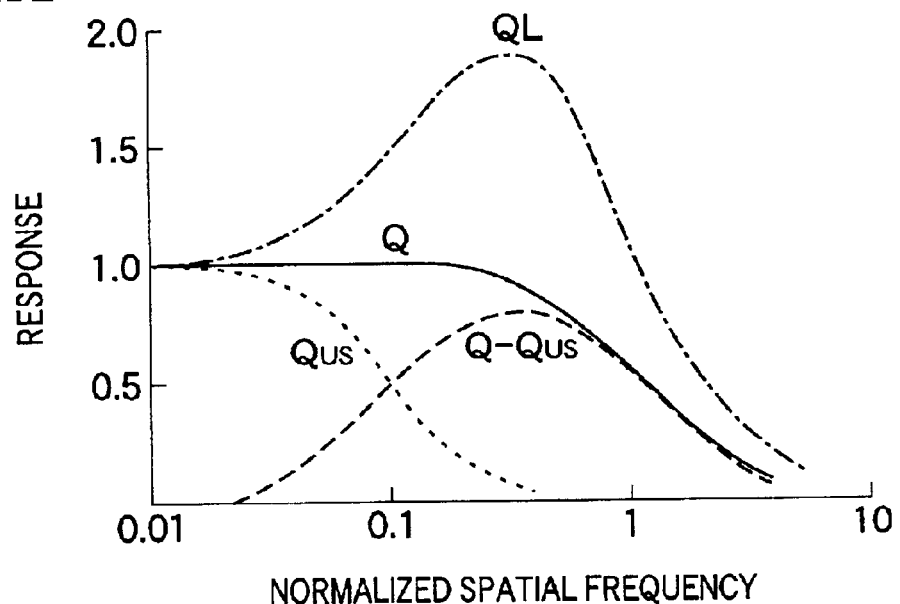
FIGS. 4A and 4B are diagrams for explaining an unsharp mask process.
Figure 4B:
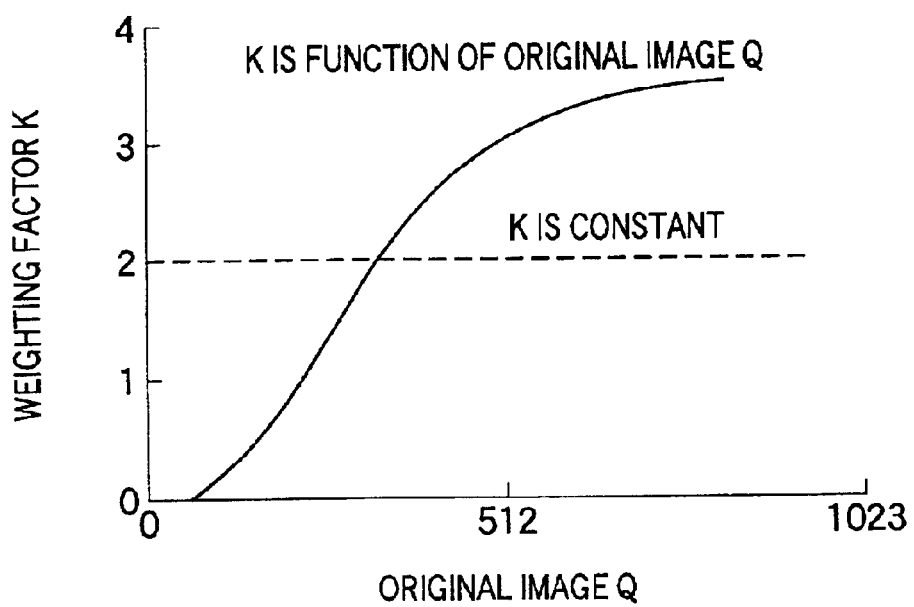

The frequency characteristics of the images are shown in FIG. 4A. The frequency of a component which is emphasized most among the frequency components of each image is determined by the size of an unsharp mask. More specifically, with a mask of large size, the response of the unsharp image decreases from a lower frequency side, and the response peaks of (Q−Qus) and QL shift onto a low frequency side, so that a low frequency is emphasized more. To the contrary, with a mask of small size, a high frequency is emphasized more. In this manner, the size of the unsharp mask is changed, whereby a frequency band important for a diagnosis can be emphasized to obtain an ultrasonic image suited for a diagnostic purpose. As shown in FIG. 4B, the weighting factor K may be either a constant or a function of the original image Q. In a case where the weighting factor K is the function of the original image Q, the response control process can be executed depending upon data values, and hence, the development of a false image or noise can be suppressed.

Next, a data analysis and normalization will be described. Since the discrepancy of respective images attributed to the difference of subjects, etc. can not be specified by the information of object only, there is sometimes a case where the optimum conditions can not be established merely by employing preset parameters and a desired image can not be obtained. Therefore, in order to prescribe the visible region of acquired image data, it is efficient to normalized data at a stage preceding the gradation control process and the response control process. The normalization is done in such a way that image data obtained by the transmissions/receptions of ultrasonic waves is analyzed to calculate normalization parameters in the image analysis unit 65 as shown in FIG. 1, whereupon a linear normalization process is executed in the image processing unit 66 on the basis of the normalization parameters calculated and a normalization rule stipulated for every body part.

A region which is analyzed by the image analysis unit 65 is a predetermined one prescribed for every body part beforehand. The analytical region is set on the basis of the information of object input from the information input unit 3. By way of example, the analytical region is the whole image, or a regular square of 10 cm around the center of the image. It is also possible to compound the analytical results of a region of a regular square of 5 cm around the center of the image at a depth of 5 cm and a region of a regular square of 5 cm around the center of the image at a depth of 15 cm.

Figure 5:
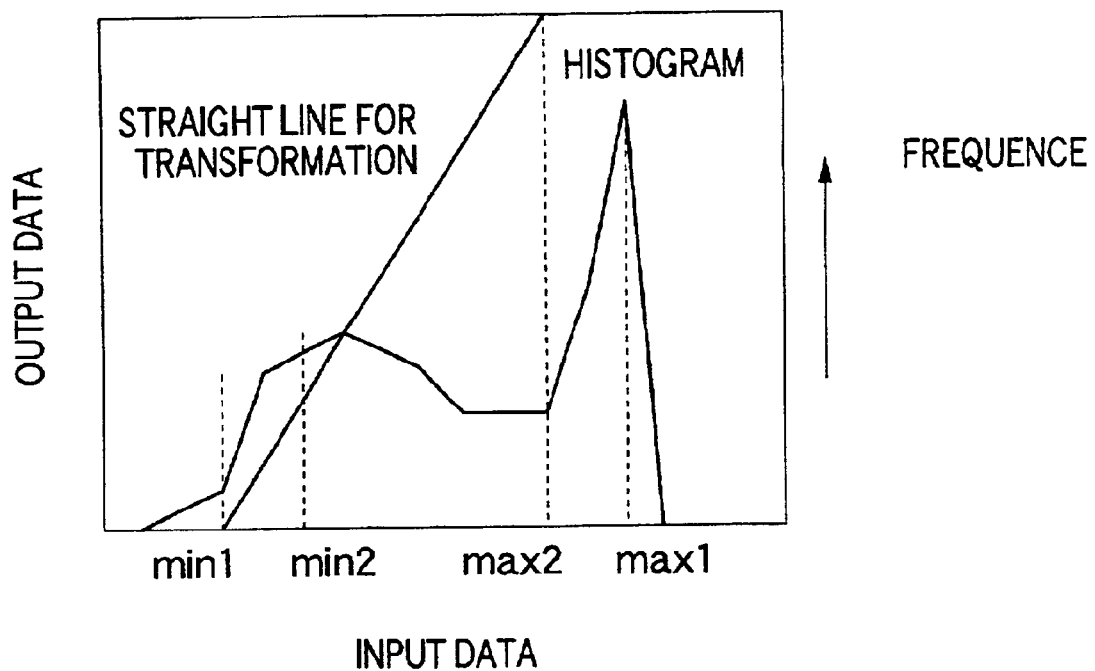
FIG. 5 is a diagram for explaining a normalization process.

The image analysis unit 65 detects peaks and calculates the normalization parameters, such as the maximum values, minimum values and average value of an intensity, by a histogram analysis. In FIG. 5, two sorts of maximum values max1 and max2 and two sorts of minimum values min1 and min2 which are used for the normalization are indicated. In conformity with the normalization rule stipulated for every body part, a linear transformation is made by way of example so that the region between the maximum value max1 and the minimum value min2 may become the full output range for the image data of the liver, and that the region between the maximum value max2 and the minimum value min2 may become the full output range for the image data of the heart. Here, the values max1, max2, etc. may be set at values which are obtained by shifting only predetermined data quantities from the maximum value of a histogram. Alternatively, by analyzing the shape of the histogram, they can be determined as the values of the positions of a second hill as reckoned from the maximum value of the histogram toward the minimum value thereof.

In selecting a frame for use in the image analysis, the following three ways are considered by way of example:

(1) There are repeated the operations of periodically analyzing frames obtained at predetermined time intervals irrespective of a position where the probe is located, so as to execute the normalization processes. In this case, a trigger signal generator is necessitated.

(2) The apparatus is caused to recognize a data acquiring scan for the analysis. A signal therefor is input from a panel or the probe. In this case, a signal input unit is necessitated.

(3) The movement of the probe is detected, and scan data on the occasion of the stop of the probe are analyzed as image analyzing data. A signal therefor is input from a panel or the probe. In this case, a sensor for detecting the movement of the probe is necessitated.

Next, examples of the settings of the parameters for the respective body parts of an object to be inspected will be described.

The liver is a body part which exists at a depth from 2–3 cm to about 15 cm, and both the focussing position and reception sensitivity of echo waves are adjusted to a medium depth region. Since the image data of the substantial region of the liver exist in a large number within a low intensity region, the gradation of the low intensity region is heightened. Since the information of a shallow region in which the level of an ultrasonic echo signal is high is unnecessary, the gradation characteristic of a high intensity region should preferably be laid down. In the ultrasonic diagnosis of the liver, the situation of thick blood vessels and the presence of growth are chiefly judged, and therefore, the emphasis of a high frequency is unnecessary in the response control process. Accordingly, the parameters are set as follows: The focussing position is set at a medium depth, the transmission power is set to be medium, the reception sensitivity has the gain of the medium depth increased, the gradation control process erects the gradation characteristic in the low intensity region and lays it down in the high intensity region, and the response control process emphasizes only a low frequency region.

On the other hand, appendicular blood vessels lie very shallow, and blood circulations in fine blood vessels need to be observed. That is, a high frequency signal in the shallow region needs to be noticed. Accordingly, the parameters are set as follows: The focussing position is set at a shallow depth, the transmission power is set to be low, the reception sensitivity has the gain of the shallow depth increased, the gradation control process lays down the whole gradation characteristic, and the response control process emphasizes a frequency region from a low frequency to a high frequency.

Figure 6:
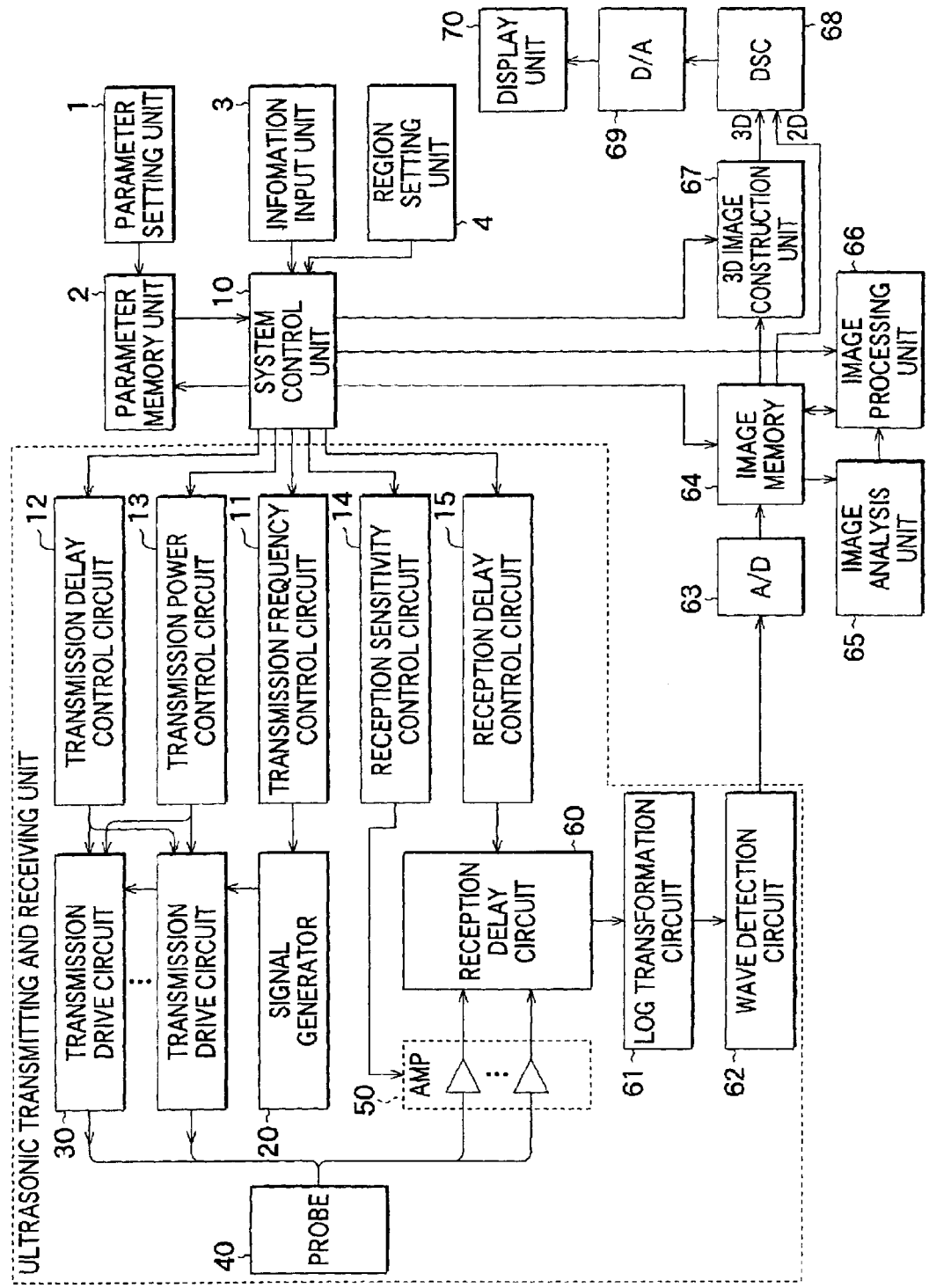
FIG. 6 is a block diagram showing the construction of an ultrasonic diagnostic apparatus according to the second embodiment of the present invention.

Now, an ultrasonic diagnostic apparatus according to the second embodiment of the present invention will be described with reference to FIG. 6. FIG. 6 is a block diagram showing the construction of the ultrasonic diagnostic apparatus according to this embodiment.

As shown in FIG. 6, a region setting unit 4 is connected to a system control unit 10, besides a parameter memory unit 2 having a parameter setting unit 1 connected thereto, and an information input unit 3. The remaining construction is the same as in the first embodiment. Here, the parameter memory unit 2 may well store parameter sets therein in correspondence with image processing rule information items which express the rules of image processing.

A desired region of interest (ROI) in a screen can be set by employing the region setting unit 4. The region of interest prescribes an image region in which image data are analyzed. The system control unit 10 determines ultrasonic transmissions/receptions conditions or image processing conditions in accordance with the results of the analysis, and parameters which correspond to the information of object or the image processing rule information input by employing the information input unit 3.

The image analysis unit 65 analyzes only the image data which are contained in the desired ROI set by employing the region setting unit 4, within the screen which is expressed by image data obtained by the transmissions/receptions of ultrasonic waves. Concretely, the image analysis unit 65 performs at least one of the calculation of normalization parameters for normalizing the image data contained in the ROI, the recognition of those positions (depths) of an object to be inspected from which received echo waves have been reflected, and so forth. The system control unit 10 controls at least one of the transmission/reception operation of the ultrasonic transmitting and receiving unit and the image processing operation of the image processing unit 66 on the basis of the analyze results of the image analysis unit 65 and the parameters which correspond to the information of object or the image processing rule information input by employing the information input unit 3.

Figure 7:
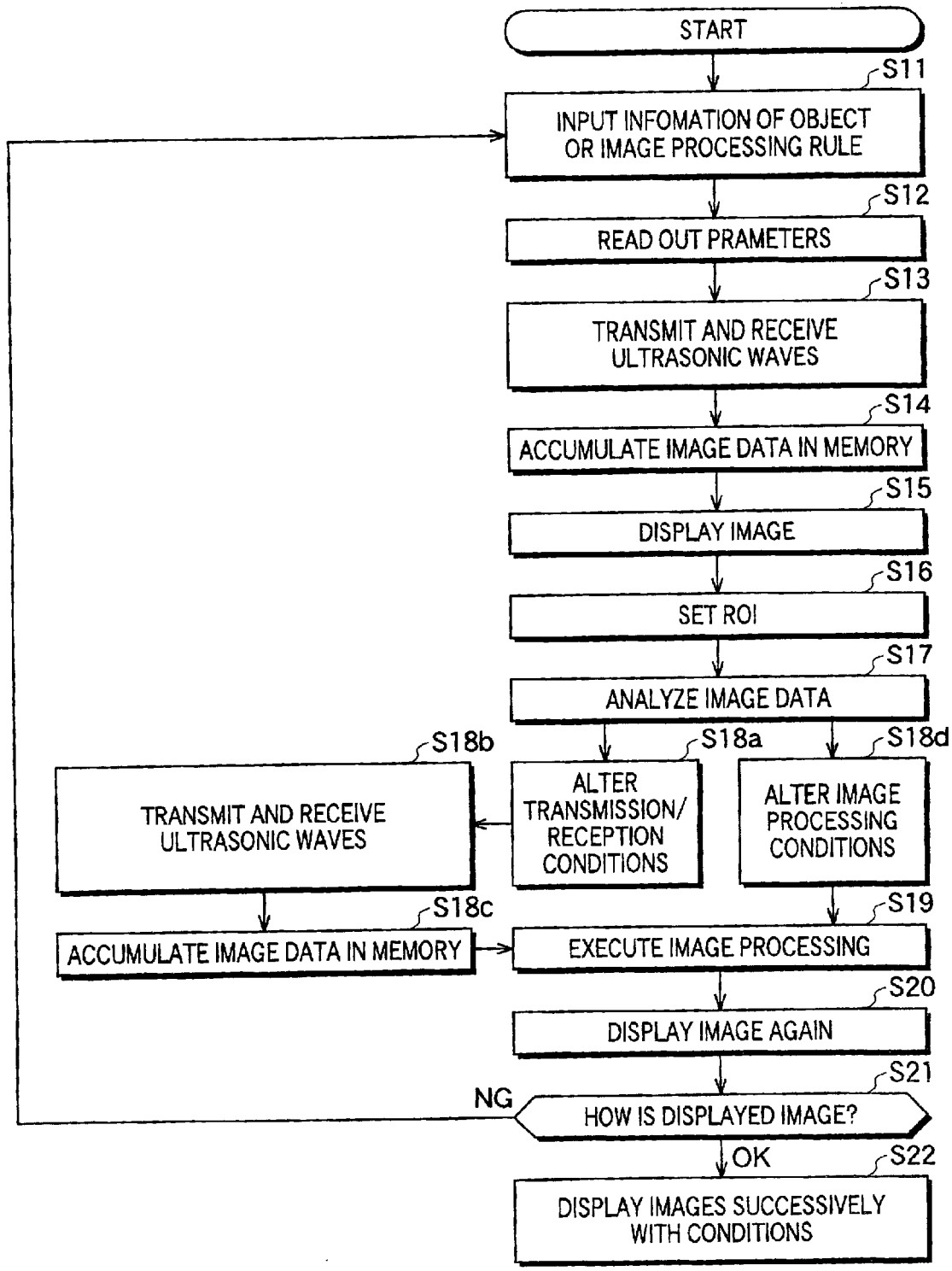
FIG. 7 is a flow chart showing an example of the operation of the ultrasonic diagnostic apparatus according to the second embodiment of the present invention.

Next, the operation of the ultrasonic diagnostic apparatus according to the second embodiment of the present invention will be described with reference to FIGS. 6 and 7. FIG. 7 is a flow chart showing the operation of the ultrasonic diagnostic apparatus according to this embodiment.

At step S11 as shown in FIG. 7, an operator inputs information of object concerned with an object to be inspected or image processing rule information on the rule of image processing, to the information input unit 3. Then, at step S12, transmission/reception condition parameters and image processing condition parameters previously stored in the memory unit 2 in correspondence with the information of object or the image processing rule information are read out by the system control unit 10.

In accordance with the transmission/reception condition parameters read out, the transmission frequency control circuit 11 controls the center frequency and frequency band of a signal to be generated by the signal generator 20, the transmission delay control circuit 12 controls the delay times of drive signals to be output from the transmission drive circuits 30, and the transmission power control circuit 13 controls the amplitudes of the drive signals to be output from the transmission drive circuits 30. Besides, the reception sensitivity control circuit 14 controls the gains of the amplifiers 50, and the reception delay control circuit 15 controls the delay times of detection signals in the reception delay circuit 60.

At step S13, in this manner, the transmission/reception conditions of ultrasonic waves such as the center frequency, bandwidth, focussing position, transmission power and reception sensitivity thereof are set in accordance with the transmission/reception condition parameters, and the ultrasonic waves are transmitted and received under the transmission/reception conditions.

At step S14, image data obtained by subjecting the detection signals to A/D conversions is accumulated in the image memory 64 in frame units. Further, the image data has its scanning format changed and its frame rate adjusted by the DSC 68, and the image data is converted into an analog signal by the D/A conversion circuit 69. At step S15, an image based on the analog signal is displayed on the display unit 70.

At step S16, the operator sets a desired region of interest (ROI) by the use of the region setting unit 4 while watching the displayed image. The setting can be made by, for example, designating the center of the region or designating a closed region with a pointer or the like. At step S17, the image analysis unit 65 analyzes the image data of an image region corresponding to the set ROI, so as to find predetermined feature quantities such as the maximum values, minimum values and average value of an intensity. At step S18a or S18d, the system control unit 10 determines either or both of the ultrasonic transmission/reception conditions and the image processing conditions in accordance with the result of the analysis in the image analysis unit 65, and the parameters corresponding to the information of object or the image processing rule information input to the information input unit 3. The conditions are altered if necessary.

In a case where the ultrasonic transmission/reception conditions have been altered at step S18a, ultrasonic waves are transmitted and received again at step S18b, and the obtained image data is accumulated in the image memory 64 in frame units at step S18c. Thereafter, at step S19, image processing is executed by the image processing unit 66. On the other hand, in a case where the image processing conditions have been altered at step S18d and where the ultrasonic transmission/reception conditions have not been altered, step S18d is followed by step S19 at which image processing is executed.

As the image processing, at least a normalization process is executed in accordance with the image processing conditions determined by the system control unit 10. Further, a nonlinear gradation control process, a response control process, scale-up/down and interpolation processes, etc. may well be executed.

Subsequently, at step S20, an image is displayed again. Here, the whole screen may be displayed, or only an image part within the ROI may well be displayed. At step S21, the operator renders a decision while watching the displayed image. If the operator is not satisfied with the displayed image, the operator may return to step S11 so as to input information of objector image processing rule information anew. In contrast, if the operator is satisfied with the displayed image, the conditions are fixed at step S22, and the images of the next frame et seq. can be successively displayed.

Conditions which can be set by various parameters, various image processing conditions, the method of a data analysis, etc. in this embodiment are similar to those described in the first embodiment.

Next, there will be described constructions in the case of employing a two-dimensional sensor array of photodetection mode for the receptions of echo waves. Four examples will be explained as the two-dimensional sensor array of photodetection mode below.

(1) Example Employing Optical Fiber Array

Figure 8:
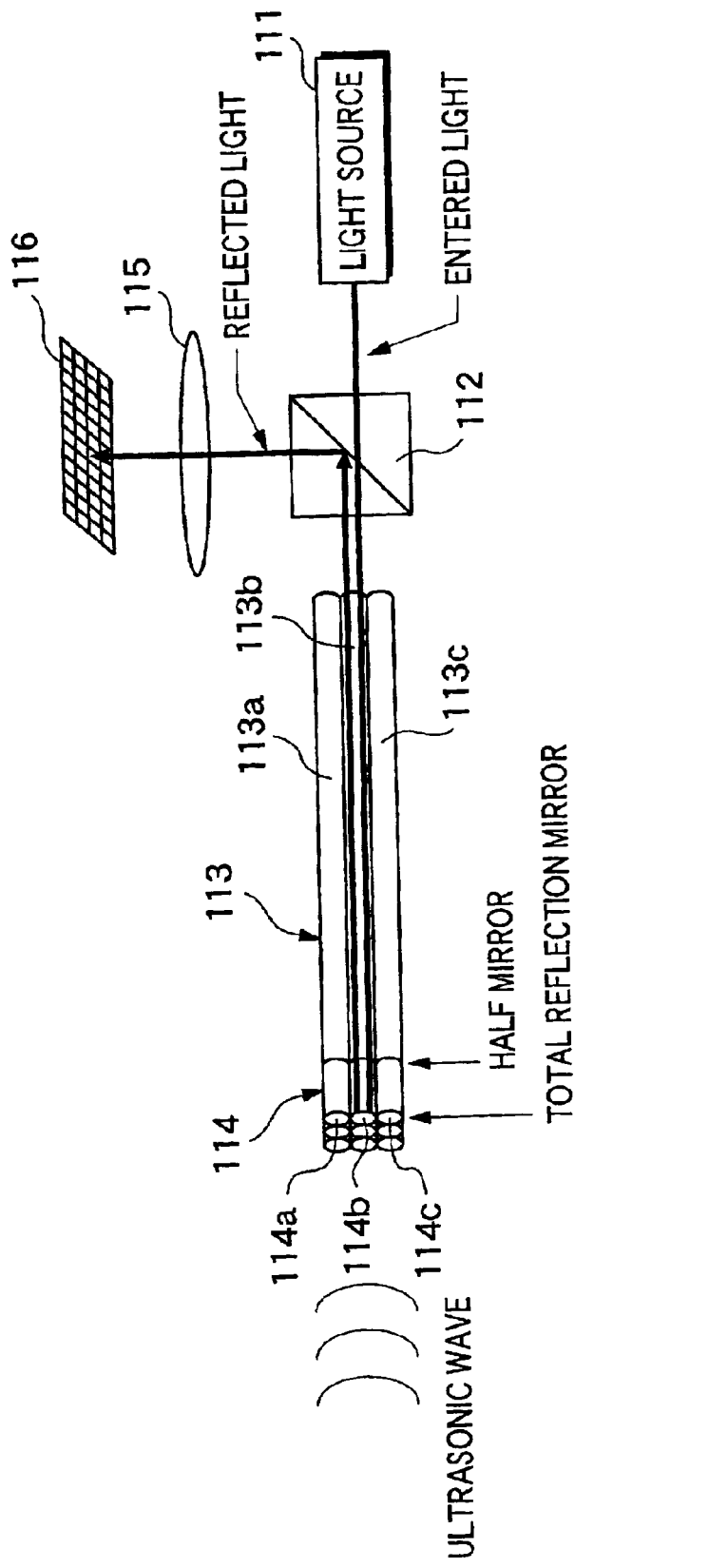
FIG. 8 is a diagram showing the first example of a sensor array of photodetection mode which can be employed in the first and second embodiments of the present invention.

FIG. 8 fundamentally depicts part of an ultrasonic diagnostic apparatus which includes the two-dimensional sensor array constituted by an array of optical fibers each being furnished with an ultrasonic detecting element at its distal end. Referring to FIG. 8, the optical fiber array 113 consists of the fine optical fibers 113a, 113b, 113c, . . . whose cross sections are arrayed in the shape of a two-dimensional matrix. Besides, the ultrasonic detecting elements 114 attached to the distal end of the optical fiber array 113 are constructed of, for example, Fabry-Perot resonators (abbreviated to "FPRs") 114a, 114b, 114c, . . . or fiber Bragg gratings which are respectively formed at the distal ends of the individual optical fibers 113a, 113b, 113c, . . . .

Light emitted from a light source 111 passes through a beam separator 112, and enters the optical fiber array 113. A light beam having entered each individual optical fiber is reflected by a half mirror (at the right end as viewed in the figure) and a total reflection mirror (at the left end as viewed in the figure) which are formed at both the ends of the corresponding FPR. Since the total reflection surface undergoes a geometrical displacement by an echo wave applied to the ultrasonic detecting element 114, the resulting reflected light is thereby modulated, and it enters the beam separator 112 again. The reflected light having entered the beam separator 112 is focussed on a photodetector 116 directly or through an optical fiber or the like, or through a focussing system 115 including a lens etc.

(2) Example Employing Optical-Heterodyne Interferometric Optical System

Figure 9:
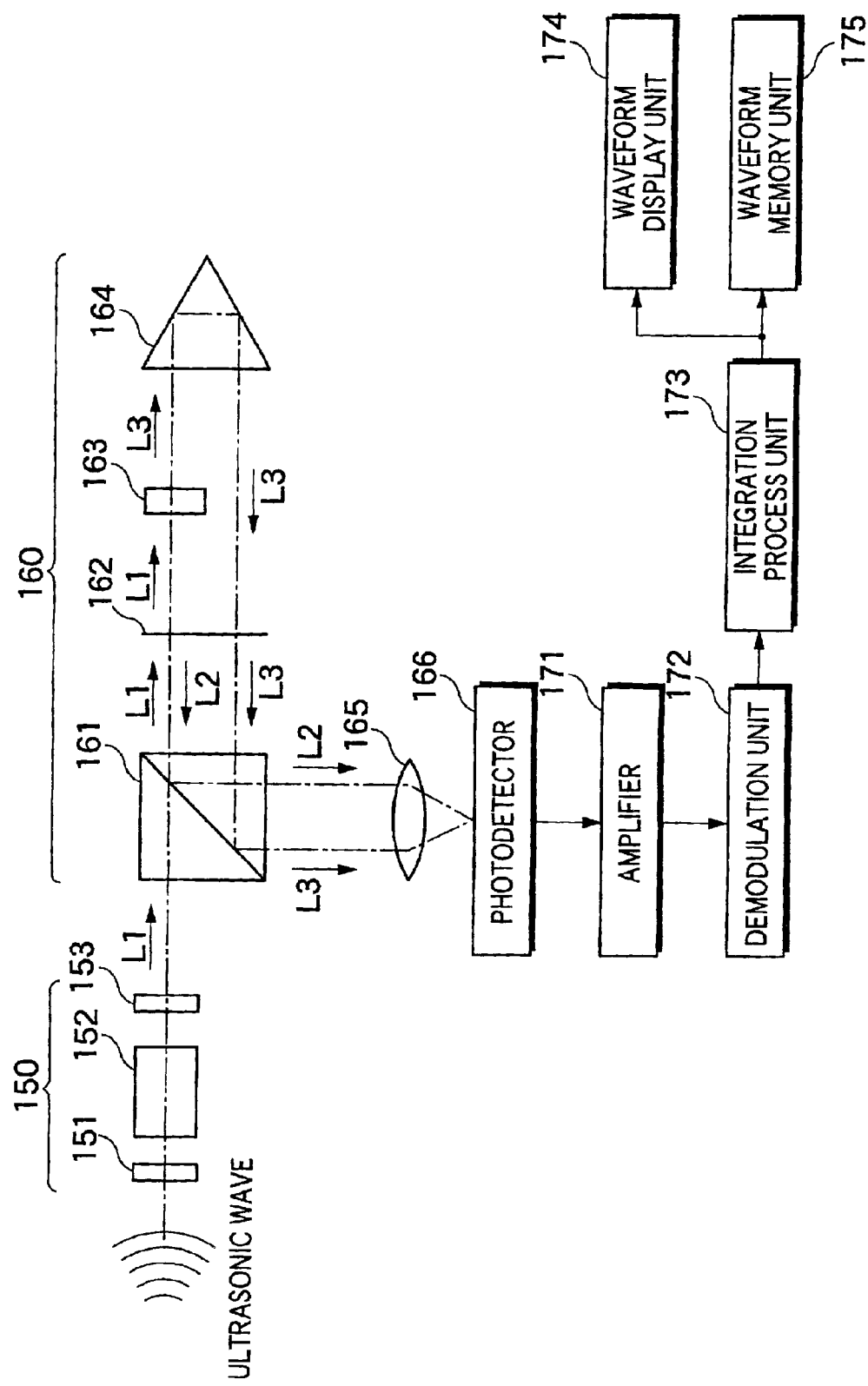
FIG. 9 is a diagram showing the second example of a sensor array of photodetection mode which can be employed in the first and second embodiments of the present invention.

FIG. 9 fundamentally depicts part of an ultrasonic diagnostic apparatus which includes the two-dimensional sensor array employing an optical-heterodyne interferometric optical system that has an optical path difference. When an echo wave enters the total reflection mirror 151 of a laser resonator 150, this total reflection mirror 151 is displaced to change the interval between the total reflection mirror 151 and transmission mirror 153 of the laser resonator 150. On this occasion, the oscillation frequency or resonance frequency of a stationary wave which develops between the two mirrors disposed on both the sides of the laser active material 152 of the laser resonator 150 changes, and also the oscillation frequency of the laser deviates. When laser radiation L1 thus emitted enters an interferometric optical system 160, a light beam L2 and a light beam L3 are generated. More specifically, the light beam L2 is generated in such a way that the laser radiation L1 is transmitted through a beam separator 161 and is reflected by a partial reflection mirror 162 as well as the beam separator 161, and it enters a photodetector 166 through a lens 165. On the other hand, the light beam L3 is generated in such a way that the laser radiation L1 is transmitted through the beam separator 161 as well as the partial reflection mirror 162, is passed through a frequency shifter 163 as well as a prism 164, is transmitted through the partial reflection mirror 162 again and is reflected by the beam separator 161, and it enters the photodetector 166 through the lens 165. An optical path difference arises between the light beams L2 and L3.

Here, when the light beam whose oscillation frequency deviates temporally enters the optical-heterodyne interferometric optical system having the optical path difference, a beat signal is generated at a frequency which shifts the variation of the oscillation frequency corresponding to a time delay component, with respect to the frequency of the original optical-heterodyne interference signal. The frequency-modulated beat signal is amplified by an amplifier 171 and is demodulated by a demodulation unit 172, and the resulting demodulated signal is integrated and processed by an integration processing unit 173. Then, the change of the frequency, that is, the waveform of the echo wave can be reproduced. This waveform is displayed on a waveform display unit 174, and is simultaneously stored in a waveform memory unit 175.

(3) Example Employing Evanescent Field

Figure 10:
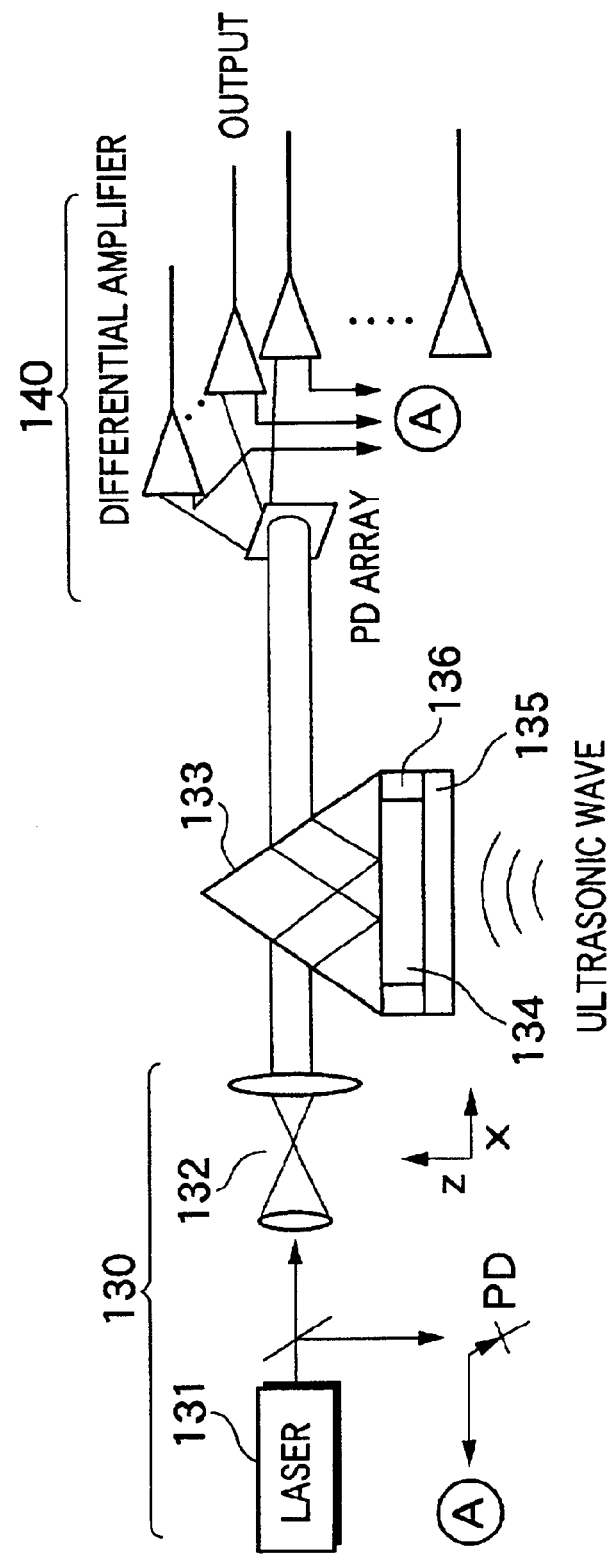
FIG. 10 is a diagram showing the third example of a sensor array of photodetection mode which can be employed in the first and second embodiments of the present invention.

FIG. 10 fundamentally depicts a part of an ultrasonic diagnostic apparatus which includes an ultrasonic transducer utilizing the phenomenon that an object existing in an evanescent field vicinal to a reflection interface is oscillated by receiving an echo wave, whereby the quantity of evanescent light changes. Referring to FIG. 10, the ultrasonic transducer is constituted by a prism 133, a gap portion 134, an optical flat 135, and a spacer 136 for defining the gap. When the echo wave enters the transducer from the lower surface of the optical flat 135, the quantity of total reflection light at the bottom of the prism 133 changes depending upon the acoustic pressure level of the echo wave. Accordingly, the spatial distribution and temporal change of the echo wave are measured in such a way that the prism bottom is illuminated with an expanded laser beam which is emitted from a light source 130 constituted by a laser resonator 131 and a beam expander 132, and that the intensity distribution of the total reflection light is read by a photodetection unit 140.

Figure 11:
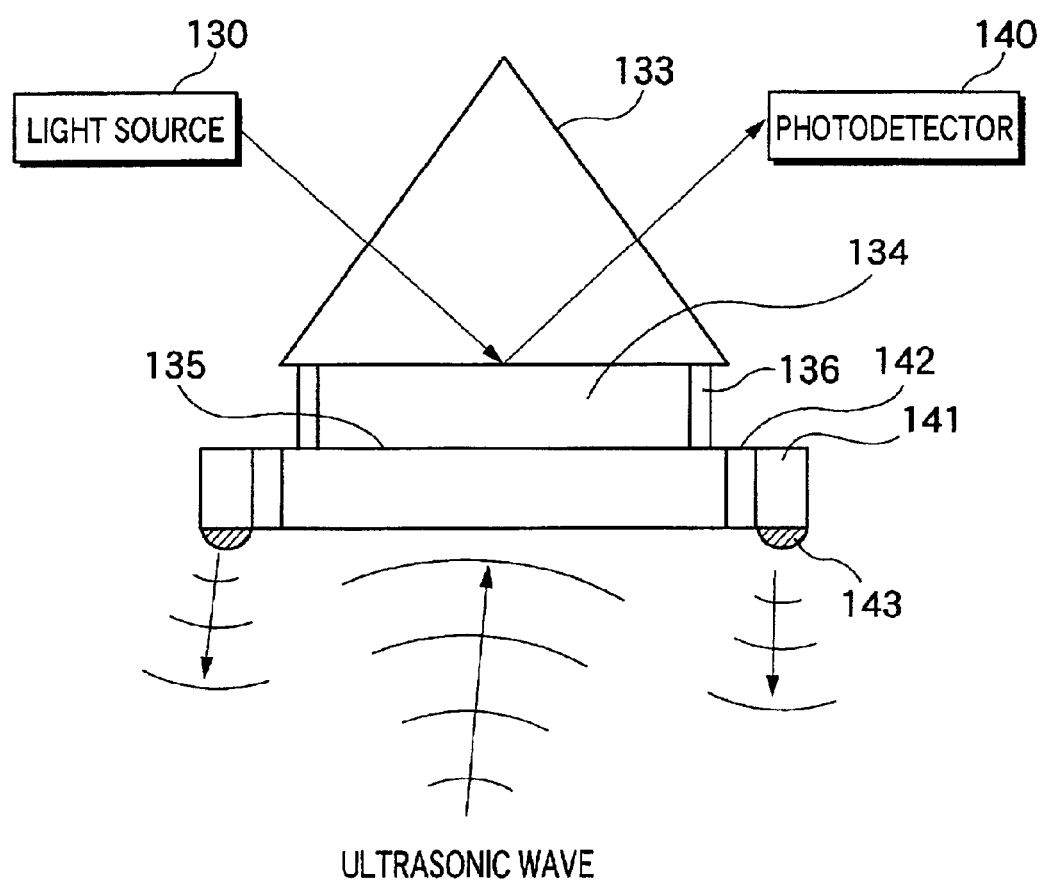
FIG. 11 is a diagram showing the fourth example of a sensor array of photodetection mode which can be employed in the first and second embodiments of the present invention.

(4) Example in which Two-Dimensional Sensor Array of Photodetection Mode is United with Ultrasonic Transmission Unit It is also considered that, since the two-dimensional sensor array of photodetection mode does not have the function of transmitting any ultrasonic wave, an ultrasonic transmitting and receiving unit is formed in a single probe by uniting the sensor array with an ultrasonic transmission unit which employs a piezoelectric device or the like. FIG. 11 shows one example of such a probe. In the example of FIG. 11, the piezoelectric device 141 made of PZT or the like is attached as the ultrasonic transmission unit to an ultrasonic transducer which utilizes the phenomenon that an object existing in an evanescent field is oscillated by receiving the echo wave, whereby the quantity of evanescent light vicinal to a reflection interface changes. More specifically, the piezoelectric device 141 made of PZT or the like is mounted on an optical flat 135 through a sound absorbing layer 142, and a focussing beam is formed by an acoustic lens 143.

The system control unit 10 as shown in FIG. 1 or FIG. 6 performs a control so as to accept the detection signals after the lapse of a predetermined time period from the start of the transmission of the ultrasonic waves. Such processes are repeated by shifting a data acceptance starting time, and data are thus acquired a plurality of times, whereby a plurality of two-dimensional frame data (surface data) can be obtained. The obtained plurality of two-dimensional frame data are accumulated in the image memory 64, and three-dimensional data is constructed in the 3D image construction unit 67 on the basis of the accumulated data.

What is claimed is:

1. An ultrasonic diagnostic apparatus comprising:
    an ultrasonic transmitting and receiving unit for transmitting ultrasonic waves to an object to be inspected and receiving echo waves reflected from the object;
    an image processing unit for executing image processing of image data, which is obtained on the basis of the echo waves received by said ultrasonic transmitting and receiving unit, by using image processing condition parameters;
    an information input unit to be employed for inputting information of object concerned with the object to be inspected;

a parameter memory unit for storing the image processing condition parameters to be used in the image processing unit, in correspondence with the information of object;

a control unit for reading out the image processing condition parameters, which correspond to the information of object input by employing the information input unit, from said parameter memory unit so as to supply the read-out parameters to the image processing unit; and a display unit for displaying an image on the basis of the image data subjected to the image processing in the image processing unit.

2. An ultrasonic diagnostic apparatus according to claim 1, wherein:

said parameter memory unit stores a plurality of image processing condition parameter sets in correspondence with one item of the information of object; and said information input unit is employed for inputting the information of object and for selecting an image processing condition parameter set from among the plurality of image processing condition parameter sets corresponding to the information of object.

3. An ultrasonic diagnostic apparatus according to claim 1, wherein the image processing condition parameters to be used in the image processing unit prescribe a control of at least one of a gradation control process, a response control process, a scale-up process, a scale-down process and an interpolation process for the image data.

4. An ultrasonic diagnostic apparatus according to claim 1, further comprising:

a three-dimensional image construction unit for constructing three-dimensional image data on the basis of the image data subjected to the image processing in the image processing unit so as to output the three-dimensional image data to said display unit.

5. An ultrasonic diagnostic apparatus according to claim 1, wherein said ultrasonic transmitting and receiving unit includes:

a plurality of ultrasonic detecting elements, arrayed in a two-dimensional shape, for modulating light entered from a light source, on the basis of the echo waves applied thereto.

6. An ultrasonic diagnostic apparatus comprising:

an ultrasonic transmitting and receiving unit for transmitting ultrasonic waves to an object to be inspected and receiving echo waves reflected from the object, in accordance with ultrasonic transmission/reception conditions which are set on the basis of transmission/reception condition parameters;

an image processing unit for executing image processing of image data, which is obtained on the basis of the echo waves received by said ultrasonic transmitting and receiving unit, by using image processing condition parameters;

an information input unit to be employed for inputting information of object concerned with the object to be inspected;

a parameter memory unit for storing the image processing condition parameters to be used in the image processing unit and the transmission/reception condition parameters to be used in said ultrasonic transmitting and receiving unit, in correspondence with the information of object;

a control unit for reading out at least either of the image processing condition parameters and the transmission/reception condition, parameters, which correspond to the information of object input by employing the information input unit, from said parameter memory unit so as to supply the read-out parameters to at least one of the image processing unit and said ultrasonic transmitting and receiving unit; and a display unit for displaying an image on the basis of the image data subjected to the image processing in the image processing unit.

7. An ultrasonic diagnostic apparatus according to claim 6, wherein:

said parameter memory unit stores a plurality of image processing condition parameter sets and a plurality of transmission/reception condition parameter sets in correspondence with one item of the information of object; and said information input unit is employed for inputting the information of object and for selecting an image processing condition parameter set from among the plurality of image processing condition parameter sets corresponding to the information of object and selecting a transmission/reception condition parameter set from among the plurality of transmission/reception condition parameter sets corresponding to the information of object.

8. An ultrasonic diagnostic apparatus according to claim 6, wherein image processing condition parameters to be used in the image processing unit prescribe a control of at least one of a gradation control process, a response control process, a scale-up process, a scale-down process and an interpolation process for the image data.

9. An ultrasonic diagnostic apparatus according to claim 6, wherein ultrasonic transmission/reception condition parameters to be used in said ultrasonic transmitting and receiving unit prescribe a control of at least one of a center frequency, a bandwidth, and a focussing position, transmission power and reception sensitivity for the echo waves.

10. An ultrasonic diagnostic apparatus according to claim 6, further comprising:

a three-dimensional image construction unit for constructing three-dimensional image data on the basis of the image data subjected to the image processing in said image processing unit so as to output the three-dimensional image data to said display unit.

11. An ultrasonic diagnostic apparatus according to claim 6, wherein said ultrasonic transmitting and receiving unit includes:

a plurality of ultrasonic detecting elements, arrayed in a two-dimensional shape, for modulating light entered from a light source, on the basis of the echo waves applied thereto.

12. An ultrasonic diagnostic apparatus comprising:

an ultrasonic transmitting and receiving unit for transmitting ultrasonic waves to an object to be inspected and receiving echo waves reflected from the object;

an image analysis unit for analyzing image data obtained on the basis of the echo waves received by said ultrasonic transmitting and receiving unit, thereby to calculate normalization parameters;

an image processing unit for executing a normalization process of the image data obtained on the basis of the echo waves received by said ultrasonic transmitting and receiving unit, in accordance with a normalization rule by using the normalization parameters calculated by said image analysis unit, and for executing image processing of the image data by using image processing condition parameters;

an information input unit to be employed for inputting information of object concerned with the object to be inspected;

a memory unit for storing the normalization rules and the image processing condition parameters to be used in the image processing unit, in correspondence with the information of object;

a control unit for reading out the normalization rule and the image processing condition parameters, which correspond to the information of object input by employing the information input unit, from said memory unit so as to supply the read-out rule and parameters to the image processing unit; and a display unit for displaying an image on the basis of the image data subjected to the image processing in the image processing unit.

13. An ultrasonic diagnostic apparatus according to claim 12, wherein:

said memory unit stores a plurality of normalization rules and a plurality of image processing condition parameter sets in correspondence with one item of the information of object; and said information input unit is employed for inputting the information of object and for selecting a normalization rule from among the plurality of normalization rules corresponding to the information of object and selecting an image processing condition parameter set from among the plurality of image processing condition parameter sets corresponding to the information of object.

14. An ultrasonic diagnostic apparatus according to claim 12, wherein the image processing condition parameters to be used in said image processing unit prescribe a control of at least one of a gradation control process, a response control process, a scale-up process, a scale-down process and an interpolation process for the image data.

15. An ultrasonic diagnostic apparatus according to claim 12, further comprising:

a three-dimensional image construction unit for constructing three-dimensional image data on the basis of the image data subjected to the image processing in said image processing unit so as to output the three-dimensional image data to said display unit.

16. An ultrasonic diagnostic apparatus according to claim 12, wherein said ultrasonic transmitting and receiving unit includes:

a plurality of ultrasonic detecting elements, arrayed in a two-dimensional shape, for modulating light entered from a light source, on the basis of the echo waves applied thereto.

17. An ultrasonic diagnostic apparatus comprising:

an ultrasonic transmitting and receiving unit for transmitting ultrasonic waves to an object to be inspected and receiving echo waves reflected from the object, in accordance with ultrasonic transmission/reception conditions which are set on the basis of transmission/reception condition parameters;

an image analysis unit for analyzing image data obtained on the basis of the echo waves received by said ultrasonic transmitting and receiving unit, thereby to calculate normalization parameters;

an image processing unit for executing a normalization process of the image data obtained on the basis of the echo waves received by said ultrasonic transmitting and receiving unit, in accordance with a normalization rule by using the normalization parameters calculated by said image analysis unit, and for executing image processing of the image data by using image processing condition parameters;

an information input unit to be employed for inputting information of object concerned with the object to be inspected;

a memory unit for storing the normalization rules and the image processing condition parameters to be used in said image processing unit and the transmission/reception condition parameters to be used in said ultrasonic transmitting and receiving unit, in correspondence with the information of object;

a control unit for reading out at least either of the normalization rule and the image processing condition parameters, which correspond to the information of object input by employing said information input unit, from said memory unit so as to supply at least either of the read-out rule and the read-out parameters to said image processing unit, and for reading out the transmission/reception condition parameters, which correspond to the information of object, from said memory unit so as to supply the read-out parameters to said ultrasonic transmitting and receiving unit; and a display unit for displaying an image on the basis of the image data subjected to the image processing in said image processing unit.

18. An ultrasonic diagnostic apparatus according to claim 17, wherein:

said memory unit stores a plurality of normalization rules, a plurality of image processing condition parameter sets and a plurality of transmission/reception condition parameter sets in correspondence with one item of the information of object; and said information input unit is employed for inputting the information of object and for selecting that a normalization rule from among the plurality of normalization rules corresponding to the information of object and selecting an image processing condition parameter set from among the plurality of image processing condition parameter sets corresponding to the information of object and selecting a transmission/reception condition parameter set from among the plurality of transmission/reception condition parameter sets corresponding to the information of object.

19. An ultrasonic diagnostic apparatus according to claim 17, wherein the image processing condition parameters to be used in said image processing unit prescribe a control of at least one of a gradation control process, a response control process, a scale-up process, a scale-down process and an interpolation process for the image data.

20. An ultrasonic diagnostic apparatus according to claim 17, wherein the ultrasonic transmission/reception conditions to be used in said ultrasonic transmitting and receiving unit prescribe a control of at least one of a center frequency, a bandwidth, and a focussing position, a transmission power and a reception sensitivity for the ultrasonic waves.

21. An ultrasonic diagnostic apparatus according to claim 17, further comprising:

a three-dimensional image construction unit for constructing three-dimensional image data on the basis of the image data subjected to the image processing in said image processing unit so as to output the three-dimensional image data to said display unit.

22. An ultrasonic diagnostic apparatus according to claim 17, wherein said ultrasonic transmitting and receiving unit includes:

a plurality of ultrasonic detecting elements, arrayed in a two-dimensional shape, for modulating light entered from a light source, on the basis of the echo waves applied thereto.

23. An ultrasonic diagnostic apparatus comprising:

an ultrasonic transmitting and receiving unit for transmitting ultrasonic waves to an object to be inspected and receiving echo waves reflected from the object;

a region setting unit to be employed for setting a desired region within a displayed image;

an image analysis unit for analyzing image data obtained on the basis of the echo waves received by said ultrasonic transmitting and receiving unit, as to the desired region set by employing said region setting unit;

an image processing unit for executing image processing of the image data obtained on the basis of the echo waves received by said ultrasonic transmitting and receiving unit;

an information input unit to be employed for inputting at least one of information of object concerned with the object to be inspected and image processing rule information concerned with a rule of the image processing;

a parameter memory unit for storing parameters concerned with at least either of transmission/reception conditions to be used in said ultrasonic transmitting and receiving unit and image processing conditions to be used in said image processing unit, in correspondence with at least one of the information of object and the image processing rule information;

a control unit for controlling at least one of transmission/reception operation of said ultrasonic transmitting and receiving unit and image processing operation of said image processing unit, in accordance with analytical results in said image analysis unit and the parameters corresponding to at least one of the information of object and the image processing rule information input to said information input unit; and a display unit for displaying an image on the basis of the image data subjected to the image processing in said image processing unit.

24. An ultrasonic diagnostic apparatus according to claim 23, further comprising:

a three-dimensional image construction unit for constructing three-dimensional image data on the basis of the image data subjected to the image processing in said image processing unit so as to output the three-dimensional image data to said display unit.

25. An ultrasonic diagnostic apparatus according to claim 23, wherein the ultrasonic transmission/reception conditions to be used in said ultrasonic transmitting and receiving unit prescribe a control of at least one of a center frequency, a bandwidth, and a focussing position, a transmission power and a reception sensitivity for the ultrasonic waves.

26. An ultrasonic diagnostic apparatus according to claim 23, wherein the image processing conditions to be used in said image processing unit prescribe a control of at least one of a gradation control process, a response control process, a scale-up process, a scale-down process and an interpolation process for the image data.

27. An ultrasonic diagnostic apparatus according to claim 23, wherein said ultrasonic transmitting and receiving unit includes:

a plurality of ultrasonic detecting elements, arrayed in a two-dimensional shape, for modulating light entered from a light source on the basis of the echo waves applied thereto.

* * * * *